(12) United States Patent
Stetter (10) Patent No.: US 6,808,618 B2
(45) Date of Patent: Oct. 26, 2004

(54) CHEMICAL SENSING APPARATUS AND METHODS

(76) Inventor: Joseph Robert Stetter, 2243 Comstock La., Naperville, IL (US) 60564

( * ) Notice: Subject to any disclaimer, the term of this patent is extended or adjusted under 35 U.S.C. 154(b) by 150 days.

(21) Appl. No.: 09/915,166

(22) Filed: Jul. 25, 2001

(65) Prior Publication Data

US 2003/0024814 A1 Feb. 6, 2003

(51) Int. Cl.$^7$ ............................................. G01N 27/404
(52) U.S. Cl. .................... 205/779.5; 205/781; 204/431; 204/412
(58) Field of Search ............................... 204/412, 415, 204/431, 432; 205/778.5, 779, 779.5, 780, 781, 782, 782.5, 783

(56) References Cited

U.S. PATENT DOCUMENTS

| | | | | |
|---|---|---|---|---|
| 3,622,487 A | * | 11/1971 | Chand et al. |
| 4,076,596 A | * | 2/1978 | Connery et al. |
| 4,172,770 A | * | 10/1979 | Semersky et al. |
| 4,525,704 A | * | 6/1985 | Campbell et al. |
| 4,571,292 A | * | 2/1986 | Liu et al. |

OTHER PUBLICATIONS

Toxic Gas CiTiceLs (pp. Tox–2–Tox–39), published before Jul. 30, 1999.*

* cited by examiner

*Primary Examiner*—Kaj K. Olsen
(74) *Attorney, Agent, or Firm*—Solomon Zaromb

(57) ABSTRACT

In an improved amperometric gas sensor, the structure, composition, and electrode potential are adjusted so as to prevent or minimize any unwanted reactivity at the counter and/or reference electrode of any analyte or interfering component of the matrix that may cross over thereto. The sensor is preferably structured so that the product of the analyte reaction at a first working electrode can be reconverted to the original analyte at a counter electrode or at a second working electrode and then reacted again at the first working electrode, with such back-and-forth reactions repeating many times, so as to yield an amplification of the analyte signal.

16 Claims, 3 Drawing Sheets

CHEMICAL SENSING APPARATUS AND METHODS

BACKGROUND OF THE INVENTION

This invention relates to improved apparatus and methods for detecting a selected chemical species, hereinafter referred to as "analyte." My invention concerns sensor devices, advances in analytical capability, and new applications of chemical sensing technology. Although the invention is directed primarily to the detection of gaseous analytes, some of its novel aspects may also apply to liquid and even solid substances.

While the present invention can have broad implications for the improvement of various types of analytical sensors, its focus is on the amperometric gas sensor, hereinafter referred to as "AGS".

The AGS has been in existence since the Clark electrode of the 50's was developed for measurement of oxygen in blood. The modern carbon monoxide [CO] sensor has existed since 1969 and resulted from the novel application of the Teflon-bonded diffusion electrode to the measurement of alcohol [ethanol] in the breath and of CO in ambient air. Subsequent improvements yielded: [a] smaller sensors, with even some micro-fabricated versions reported; [b] wick or matrix electrolytes with improved lifetime and reduced attitude-sensitivity; [c] applicability to a number of new analytes besides $O_2$, ethanol, and CO; and [d] more cost-effective manufacture. Also, during the last 30 years, the AGS has become increasingly important in industrial, medical, and environmental applications and has become one of the most successful and widely used chemical sensors.

The AGS is useful in numerous applications, such as medical oxygen measurement, environmental analysis, or toxic gas detection, including home CO alarms and personal toxic gas alarms used to protect human health and the environment on a daily basis. The gases that have been most significant commercially in the repertoire of the AGS include but are not limited to CO, oxygen, $H_2S$, NO, $NO_2$, $SO_2$, monomethylhydrazine, ethanol, and many others. Table 1 gives a few examples of the electrochemical reactions that have been proposed for some typical analytes. There are commercially available AGSs for many of these analytes and many more are possible. High temperature versions of the AGS using solid electrolytes further expand the applications of these sensors to automotive uses.

TABLE 1

Amperometric Gas Sensors can address a variety of analytes.

Many electrochemically reactive molecules can be detected.

OXIDATIONS: $R ==> X + ne^-$ [1]
where R may be $N_2H_4$, $SO_2$, $C_2H_5OH$, $C_2H_2$, $NH_3$, $H_2$,
NO, or HC . . . and X is the corresponding oxidized species REDUCTIONS: $X + ne^- ==> R$ [2]
where X may be $O_2$, $O_3$, $Cl_2$, $Br_2$, $I_2$, or $NO_2$, . . .
Proposed Working Electrode Half-Cell Reactions Include:

$CO + H_2O ==> CO_2 + 2 H^+ + 2 e^-$ [3]
$H_2S + 4 H_2O ==> SO_4^{2-} + 10 H^+ + 8 e^-$ [4]
$NO + H_2O ==> NO_2 + 2 H^+ + 2 e^-$ [5]
$NO_2 + 2 H^+ + 2 e^- ==> NO + H_2O$ [6]
$½ O_2 + 2 H + 2 e^- ==> H_2O$ [7]

Today, such sensors have typical sensitivities in the range of parts per million [ppm] to parts per billion [ppb] by volume. This is the typical limit of detection for simple chemical sensors. Such sensors usually comprise: [a] a working electrode [WE] at which the analyte gets consumed by a half-cell reaction such as those listed in Table 1; [b] a counter electrode [CE] for a complementary half-cell reaction; and [c] a reference electrode [RE], which serves to control the electrochemical potential of the WE, and all three electrodes are in electrolytic contact, with the WE designed to be exposed to the analyte-containing gas sample. The CE and RE are sometimes combined to form a single counter and reference electrode, CE/RE. The term "auxiliary electrode" is sometimes used to refer to the CE or CE/RE. Present limitations to sensitivity and selectivity are tied to signal size, noise, drift, and background current of the sensor and ultimately to the choice of: 1) materials used for electrocatalysts [electrodes] and electrolytes, and 2) structure [geometry] and methods of operation of the sensor. Most of the efforts to-date at improving the sensitivity and selectivity of an AGS were focused on the composition of the WE and on its geometrical structure and arrangement relative to the RE and CE.

To reduce the detection limit of an AGS to much lower analyte concentrations, e.g., to as low a range as parts per quadrillion [ppq] by volume, my invention focuses on the composition, structure, relative arrangement and operation of the CE, and/or the RE, so as to: a) greatly enhance the selectivity of an AGS to specific analytes by minimizing spurious signals from interfering species; and b) increase its sensitivity by orders of magnitude through amplification of signals due to any selected analyte.

The closest publication akin to my amplification concept is that of F. R. Fan and A. J. Bard, in *Science*, Volume 277, Pages 1791–1793, 1997, wherein a redox molecule is trapped and cycled in a tiny volume of liquid. Other partly relevant work involves the use of more than one electrode in capillary electrophoresis [F.-M. Matysik et al., "Application of microband array electrodes for end-column electrochemical detection in capillary electrophoresis," *Analytica Chimica Acta*, 385, 409–415, 1999] and in other all-liquid systems [O. Niwa et al., Electrochemical Behavior of Reversible Redox Species at Interdigitated Array Electrodes with Different Geometries: Consideration of Redox Cycling and Collection Efficiency,"*Anal. Chem.*, 62 447–452, 1990], wherein the first electrode does oxidation and the second does reduction to get selectivity improvements; but these are akin to the rotating ring disk situation for electrochemical studies wherein selectivity or reaction products are confirmed. None of these prior publications includes repeated amplification of a signal from an analyte in a gaseous medium, as described herein.

OBJECTIVES

It is an object of my invention to effectuate improvements in gas detection wherever additional sensitivity and/or better selectivity may be required.

A significant improvement in the AGS should benefit not only its existing applications but also make possible many new uses. Specific new benefits could range from improving the treatment for neonatal jaundice to discovering unexploded ordnance or contraband drugs. It is therefore an object of my invention to provide a sensor with femtomolar sensitivity and high selectivity, which can be micro-fabricated and is inexpensive, robust, and consuming minimal power, for many applications in medicine, environment, and industry, including automotive uses.

It is an object of my invention to provide radically new sensor designs that will advance the science and art of chemical sensing, including electrochemistry, amperometry, catalysis of gas phase electrochemical reactions, and chemical sensors, in a significant manner.

An object of this invention is to utilize new sensor structures and geometries to achieve million-fold or larger improvements in the analytical sensitivity of the AGS.

Another goal of my invention is to provide a simple and inexpensive "chemically-amplified" AGS.

An object of the invention is to create chemical sensors that can amplify a minute change so that low concentrations of analyte can be detected by a single tiny chemical sensor.

These objectives are further tied to industrial interests by their applicability to $NO_x$ sensing and their potential to vastly improve sensor specifications for automotive uses.

It is another object of my invention to provide better sensors leading to improved analytical instruments which will impact various fields of science and engineering with cost-effective analytical tools for medical, environmental, and materials research, development, and applications.

In biological areas, NO is important in the study of neuron function and CO in the breath of neonates is an indicator of jaundice. Current techniques are expensive or cumbersome, and a simple and selective AGS for these compounds would provide significant benefit. It is therefore a specific object of my invention to provide ultra-sensitive AGSs having the ability to measure trace concentrations of NO and CO.

Current CO sensors are not quite adequate for fuel cells, home CO alarms, and micro-noses, and a better sensor would benefit society. Gas sensors are becoming more commonplace in industry and society for safety, health, and environmental measurement and control. Gas sensors in the long run will become widely used in many more places, such as elevators, buildings, cars, homes and the like, to provide for improved human health, safety, and comfort. Gas sensors will lead to better process and products instrumentation and control. Critical applications like humanitarian de-mining or detection of explosives at airports are not possible with present chemical sensors, indeed with any sensors or analytical instruments, and still rely on the imperfect but elegantly sensitive dog's nose. In order to rival such sensitivity, an improvement of several orders of magnitude is required in the present AGS. It is therefore still another object of my invention to provide detectors that mimic the dog's nose and are millions of times more sensitive than current systems.

The present CO sensor is difficult to use for stack gases and fuel cell automotive vehicles because it has cross sensitivity to many other pollutants and cannot operate effectively above 60° C. The present CO sensor lacks ability to be used on very small samples with high sensitivity and stability and cannot be easily used in the treatment of jaundice in newborn infants. Therefore, it is an object of my invention to provide an AGS with improved sensitivity and selectivity for CO that could make these applications possible.

It is yet a further object of my invention to provide an improved $NO_2$ and NO sensor that is inexpensive and of small size and weight, has extremely high sensitivity, and consumes little power, that could contribute to better physiological measurements of NO or to better measurements of NO and $NO_2$ in environmental and automotive applications.

It is yet another object of my invention to provide an improved AGS which can yield analytical devices that are portable, inexpensive, and have the potential for microfabrication.

More objects of the invention will become apparent to professionals in the industrial safety and hygiene, environmental, law enforcement, health monitoring, chemical, metallurgical, and related areas following perusal of the complete specification.

BRIEF SUMMARY OF THE INVENTION

A key feature of my invention is that it focuses primarily on the CE and/or RE rather than on the WE, in distinction from what was done in most previous advances in AGS technology.

Briefly, my invention effectuates major improvements in the AGS through the following modifications:

1. Adjustments in structure, composition, and electrode potential which result in minimal or no reactivity of any analyte crossing over to the CE and/or RE, preferably combined with maximal reactivity of the CE to the product of the analyte reaction at the WE; and 2. A structural arrangement of the CE relative to the WE whereby the product of the analyte reaction at the WE can be reconverted to the analyte at the CE and then reacted again at the WE, with such back-and-forth reactions repeating many times, so as to yield an amplification of the analyte signal; or 3. Alternatively, a structural arrangement whereby said reconversion of the analyte reaction product occurs at a second WE rather than at a CE.

BRIEF DESCRIPTION OF THE DRAWINGS

The invention is best explained with reference to the drawings, in which.

DETAILED DESCRIPTION OF THE INVENTION

Figure 1:
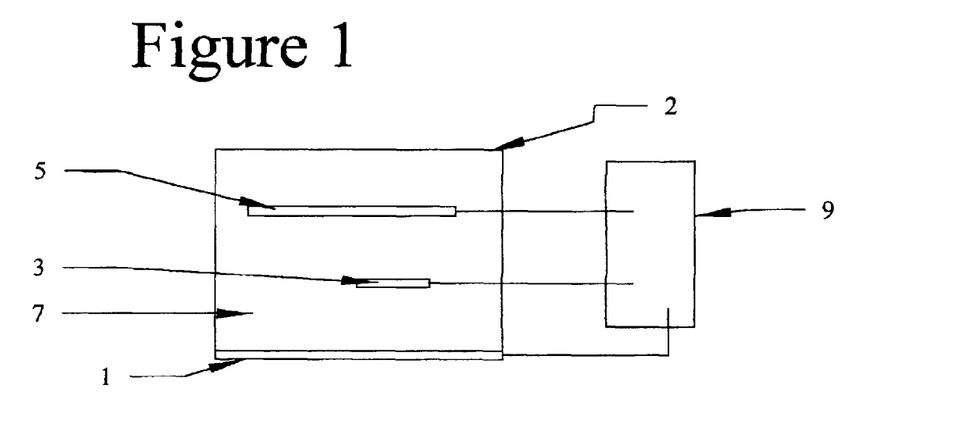
FIG. 1 is a schematic diagram of an amperometric gas sensor [AGS], including one preferred embodiment of my invention.

As shown in the schematic diagram of FIG. 1, a typical AGS comprises a working electrode [WE], 1, a reference electrode [RE], 3, and a counter electrode [CE], 5, in contact with an electrolyte, 7. While the primary concern is with room temperature amperometric gas sensors, an obvious extension includes the high temperature zirconia solid electrolyte amperometric sensors for automotive exhaust, stack gas or other high temperature applications. Taking the example of FIG. 1 for a CO sensor, the three electrodes 1, 3, and 5 are in contact with electrolyte 7 to make an electrochemical cell. A porous hydrophobic membrane [not shown] which allows the gaseous CO analyte to reach the WE while containing the electrolyte within the cell, defines a compact area to construct a triple phase boundary in the WE, 1, where analyte is consumed by the electro-oxidation Reaction 3 of Table 1 and produces 2 electrons per CO molecule that flow into an external potentiostating and amplifying circuit, 9, to provide an amplified sensor signal. To balance the electrochemical cell, the CE, 5, sometimes also called "auxiliary electrode," runs an opposed electro-reducing half-cell Reaction 2 which is partly controlled by a potentiostat in circuit 9. In some AGS devices, the CE and RE may be combined into a single counter and reference electrode.

The overall mechanism to generate the sensor signal from the analyte half-cell reaction consists of the following steps:

1] Analyte is transported to the sensor inlet which may or may not contain a filter to enhance selectivity by removal of interfering reactive non-analyte compounds, hereinafter referred to as "interferences".
2] Analyte is transported across a porous membrane to a triple WE/electrolyte/gas interface.
3] Adsorption at the WE and electrocatalytic reaction at the triple-phase boundary [e.g., Reaction 1 of Table 1, which produces 2 electrons per CO molecule].
4] An opposed complementary half-cell reaction occurs at the CE.
5] Products diffuse away from the interface and the electrons are conducted away in the external circuit 9.

To prevent or minimize sensor responses to possible interferences, special attention must be paid to the compositions of the interconnecting electrolyte 7 and electrodes 1 and 5 and to the electrochemical potentials of the WE and CE. The composition of electrolyte 7 can be an important determinant of selectivity. Several brief examples serve to illustrate this point. The current AGSs for hydrazine are based on a system with a basic electrolyte because poor or no signals are observed in acids with the same catalyst and electrode potentials. This is because the protonated form of the hydrazine, $N_2H_5^+$, that is formed in the acidic electrolyte has a different electrochemistry than the molecular form, $N_2H_4$, that would exist in neutral or basic solutions. Another example is the present $H_2S$ sensor which utilizes a gold electrocatalyst yielding low signals for CO. The electrochemical oxidations of both CO and $H_2S$ are favored at anodic potentials but the catalytic reaction of CO on Au is thousands of times slower than it is on Pt while the $H_2S$ reaction remains fast on either Au or Pt. Therefore, Au provides a level of selectivity between CO and $H_2S$ based upon the kinetics of the electrode reactions. A low-surface-area gold electrode offers the best selectivity for $H_2S$ sensors. An example of thermodynamic selectivity is given by the reaction of $NO_2$ at potentials which are cathodic [e.g., 0.8 volt versus the RHE (reversible hydrogen electrode)] to the oxidation wave of NO, so that we can observe the $NO_2$ reduction signal even in the presence of high concentrations of NO. These examples illustrate the importance of materials selection for electrodes and electrolytes, as well as geometry and the support housing configuration. We will continue with our description of the art so that the innovation we describe here is easier to illustrate.

In the current sensor, the electrolyte 7 may be 4 M $H_2SO_4$. However, elevated temperatures require a temperature-stable electrolyte such as Nafion or Nasicon, a cation- or anion-exchange electrolyte, or crystalline or quasi-crystalline solid ionic conductors, such as zirconia. Alternatively, a non-aqueous electrolyte [e.g., propylene carbonate/lithium perchlorate] may be used. The non-aqueous system has very different solubility parameters and therefore totally different selectivities for gas analysis. Here we may include other gases besides CO, such as $H_2S$, NO, $NO_2$, and $SO_2$, because of their analytical importance.

For automotive applications the Nafion, Nasicon, or zirconia type electrolyte is preferred because of its capability to operate at high temperatures, which is a requirement. Separate sensors with different catalysts and electrolytes may be fabricated for improved selectivity.

In the case of the most common ambient temperature AGS, the CO sensor, the electrolyte 7 is 4 M $H_2SO_4$, and the same Pt-black catalyst used in 1969 for ethanol and CO is still used today for all three electrodes 1, 3, and 5. The three electrodes are sealed or otherwise bonded to a cell body 2 so that they are in electrolytic contact with each other. Typical AGSs, especially those for CO, have the CE and RE fairly close to each other and to the WE, as shown in the cross-sectional diagram of FIG. 2A. The construction of the modern AGS of this type hinges around the development of the Teflon-bonded fuel cell electrode. The WE electrocatalyst is a composite Teflon-catalyst mixture bonded to one side of a gas-permeable electrolyte-impervious hydrophobic Teflon membrane. The WE composite membrane serves several purposes by being hydrophobic to keep the electrolyte from leaking out while at the same time providing a porous gas path to the high-surface-area electro-catalyst for efficient reaction of the analyte. The amount of Teflon in the electro-catalyst layer is carefully adjusted for maximum performance of the sensor. The composition must contain sufficient Teflon to bind the catalyst particles together and to the membrane, providing structural rigidity. Yet it is important to minimize the amount of the insulating Teflon binder so as to maintain a high electrical conductivity. An optimum value of Teflon retains porosity and maximizes the triple phase boundary [solid catalyst, liquid electrolyte, and gas analyte] where the reaction occurs fastest. From the electrochemical point of view, the process of signal generation in such a sensor can be seen to be a function of the geometry or structure of the sensor as well as of the materials chosen for the electro-catalytic reaction. Hence this invention is partly focused on new materials tin electrodes and on novel structures or geometries. The generic mechanism presented above is at least conceptually applicable to most if not all AGS types and is well known. Some variations of this structure are also possible. The placement of the electrode onto a solid polymer electrolyte [e.g., Nafion] eliminates the need for the Teflon membrane. Such structures have been microfabricated and produced sensors with very fast response signals for NO and $H_2S$.

Figure 2A:
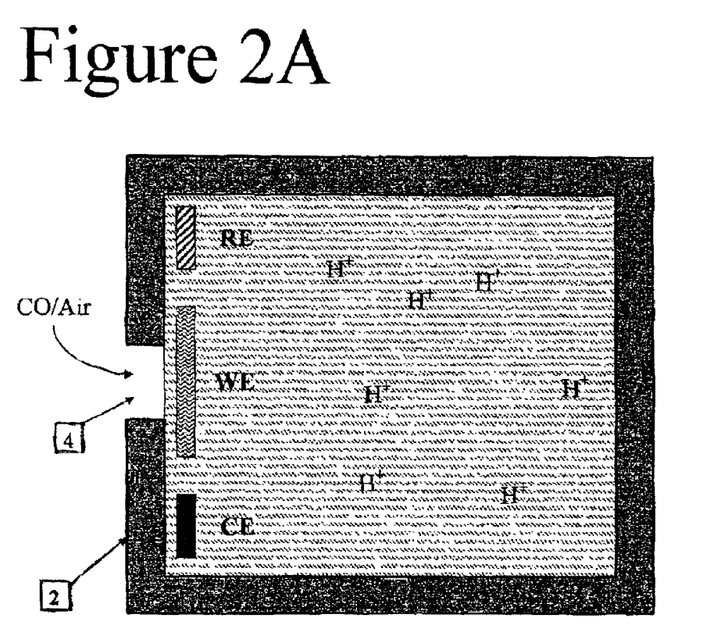
FIG. 2 presents a comparison of the cross-sectional views of a typical presently manufactured CO sensor [FIG. 2A] and of an improved CO sensor [FIG. 2B] according to a preferred embodiment of my invention.

As shown in FIG. 2A, the usual CO sensor has a small hole, 4, for gas access. One can calculate the amount of gas entering the hole and the expected current using Faraday's Law for the Reaction 3 of Table 1. The calculation typically yields a measured current efficiency that is below 100%, which suggests that not all of the CO reaching the WE is oxidized. An alternative explanation is that some of the CO gets to the CE and/or RE [we will use the term CE/RE to mean the CE and/or the RE] where it reacts, thereby decreasing the "efficiency" of the cell to perform the singular task of anodic oxidation of the CO. An occurrence at the CE/RE of both the oxidation Reaction 3 and a complementary reduction such as Reaction 7 would represent a short-circuited consumption of analyte without a measurable CO signal or a drift of the RE potential or some other combination effect of the sample and the CE/RE. These side reactions of the analyte at the CE/RE are measurable and cause the observed WE reaction to be interfered with, as this can be easily measured. It is therefore important that the cell only perform the singular electro-oxidation or electro-reduction of the analyte at the WE so that the analytical signal represent in the most efficient manner the concentration of the analyte in the sampled gas and that interactions at the CE/RE of the sampled analyte-containing matrix have no observable participation or effect on the WE signal.

An experimental observation of mine made with typical CO sensors also logically extends to other analytes. When the cross-sectional area of the hole 4 was quadrupled by doubling its radius, the analytical signal should then have increased fourfold, whereas typically the signal was only twice as great, indicating that some of the CO was reaching and reacting at the CE. The enlarged hole brings the CO closer to the CE, and so the diffusion path to get to the CE is shorter, making the crossover of analyte greater and thus not scaling the output as expected.

In some situations, this could be a fatal flaw. For certain CO sensor designs, the occurrence of Reaction 3 at the CE with a complementary Reaction 7 or its equivalent at the WE could cancel or annihilate the analyte signal at the WE, i.e., the sensitivity of the AGS would decrease to zero. If such a sensor were to serve as an alarm, the alarm would not activate, and since CO is toxic and flammable, an accident could occur causing loss of human life and property.

This has not yet occurred in practice because in most sensors there is an asymmetry for the access of the analyte to the WE and CE/RE both because of the geometry [symmetry of the air exposure situation] and/or the catalytic activity [smaller electrode with less catalyst]. However, such instability in the sensitivity has been noticed from time to time although it was never explained in the literature or in private discussions until this disclosure of my invention.

Therefore, one preferred embodiment of my invention is to render the CE inaccessible to or inactive toward the analyte by one of the following means:

A. Proper adjustment of its electrochemical potential, e.g. to <+0.8 Volt versus RHE for CO sensors; or B. Making the CE/RE from a different material, e.g., for CO sensors having the CE/RE catalyst comprise Ir or oxides of Ir, Au, Pb/$PbO_2$, Ag/AgCl, Ru, Pd, low-surface-area (e.g., vapor-deposited) Pt or any other substance at which electro-oxidation of CO is hindered; or C. Treating the CE/RE to reduce its catalytic activity toward the analyte, e.g, for CO sensors, electro-oxidizing at 1.4 Volt versus RHE to convert the Pt black surface to PtO; or poisoning the CE/RE catalyst [e.g., immersing the CE/RE in 500 ppm CO for several days before including it in a CO sensor]; or D. Forming a barrier which prevents or minimizes access of analyte to the CE/RE, e.g., comprising a coating with a gas-impermeable ionic conductor such as Nafion or Nasicon or a scavenger material or electrode at which the analyte reacts before it can reach the CE/RE, or creating a barrier at the entry of the sensor so the unwanted gas cannot enter the cell at all to react at the CE/RE; or E. Interposing a lengthy path through the electrolyte between the WE and the RE and/or CE; or F. Exposing the CE/RE to a gaseous or liquid reagent which results in the predominance of a complementary reaction at the CE to the exclusion of the analyte reaction.

Figure 2B:
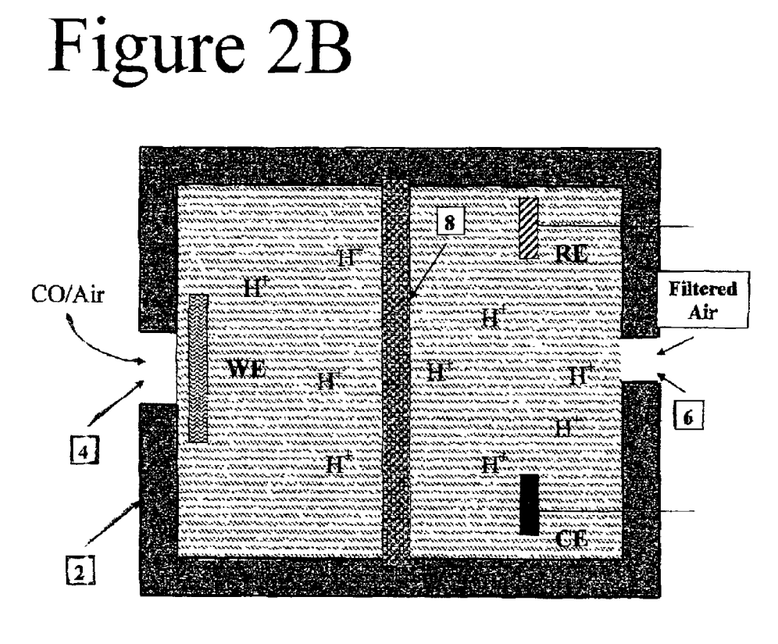

The cross-sectional view of FIG. 2B illustrates the separation of the CE and RE from the sampled air inlet by a barrier 8, which may be made of fitted glass or of Nafion, and the introduction of a second hole 6 through which filtered, analyte- and interference-free air may be introduced into the CE/RE compartment for the oxygen reduction reaction 7 to proceed unabated. The feeding of filtered air to the CE/RE through a separate hole is applicable not only to the CO sensor of FIG. 2 but to any other AGS wherein the analyte is oxidizable.

Two examples of improvements that incorporate the above strategy and are new can now be presented. First is a CO sensor with the RE replaced by a Ag/AgCl electrode which can act in concert with a Pt-catalyzed CE or act as the CE and RE of the cell. This new configuration eliminates the $H_2$ interference to which current designs are vulnerable. In addition, it eliminates interference from CO drifting to the CE/RE, which especially occurs in current cells at high CO concentrations and is observed at best as a non-linearity of the signal and at worst as elimination of the CO signal, as described above. Both of these are critical advantages in some cases and represent a unique capability for this novel CO sensor. Second is a hydrogen sensor which illustrates the incorporation of two of the above approaches simultaneously. The novel $H_2$ sensor has a Ag/AgCl RE/CE or just RE and a CE of Pt wire, and further has a solid 0.002"-thick FEP Teflon barrier at the entrance to the cell. The role of the FEP Teflon barrier is to substantially eliminate CO and other interfering gases from the cell altogether while allowing sufficient $H_2$ to pass into the cell for measurement. The role of the Ag/AgCl electrode is to be substantially free of the cell failure caused by the above deleterious reactions of $H_2$ or any other matrix gas at the CE/RE. This configuration allows for the first time the accurate, drift-free measurement of $H_2$ with an AGS that is also insensitive to CO in the sampled gas. These two novel examples illustrate the approach and its value in performing quantitative and qualitative analysis with an AGS. We have cited the CE/RE examples and continue with additional structural and method examples below.

Figure 3:
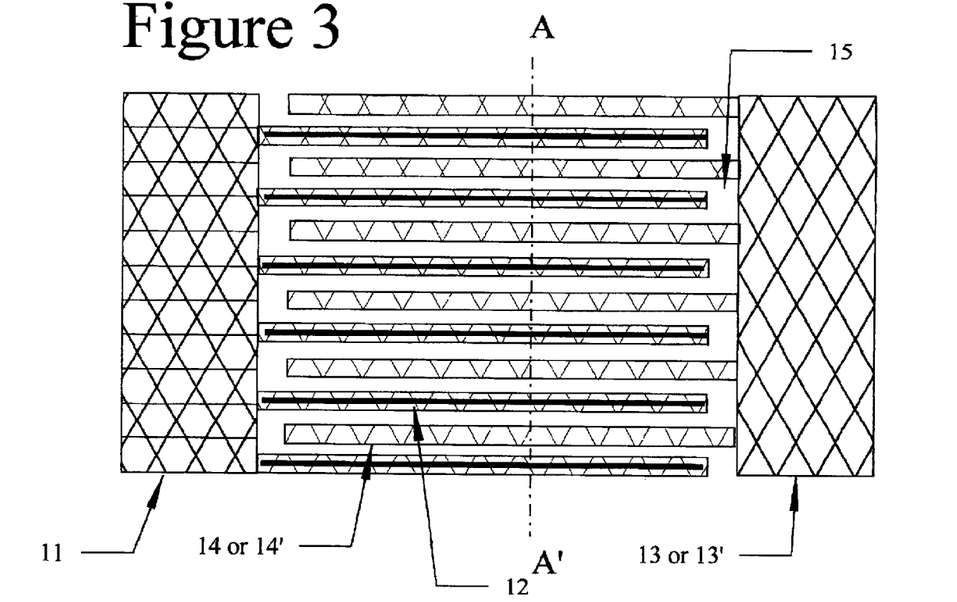
FIG. 3 is a schematic block diagram of other preferred embodiments of my invention.

FIG. 3 represents a basic design of chemical sensors that are able to amplify their signal for an analyte giving rise to greater sensitivity and greater selectivity.

Further preferred embodiments of my invention can be best explained with reference to FIGS. 3–6. In FIG. 3 are shown two interdigitated electrodes 11 and 13 with their respective digital extensions 12 and 14 separated by a narrow maze-shaped gap or channel 15 which is filled with a gaseous test sample. The tested gas may flow either along the length of the digital extensions or perpendicularly thereto. Note that the electrodes must have a thin coat of electrolyte to keep them in ionic or electrolytic contact with each other and with the CE/RE of the cell/sensor.

Figure 4:
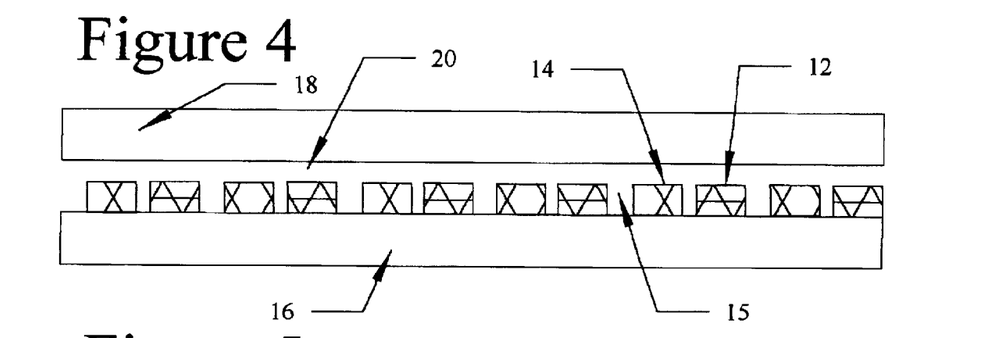
FIG. 4 is a schematic view of Section A—A' of FIG. 3 in one of said preferred embodiments.

FIG. 4 is a schematic view of Section A—A' of FIG. 3 representing one embodiment of the invention. Here the electrode 11 with its digital extensions 12 is a WE of an AGS, whereas the electrode 13 with its extensions 14 constitutes the CE. However, in this instance, the extensions 14 of the CE are fully exposed to the test gas, as are the extensions 12 of the WE. The digits 12 and 14 are in electrolytic contact with an ionically conductive solid electrolyte, such as the cation-exchange resin Nafion or an anion exchanger, which also serves as a mechanical support for the electrodes and as one of the cell walls confining the test gas. An opposite confining cell wall 18 may be made of a gas-impervious material, such as non-porous Teflon, polyethylene, polyacrylate or glass. Cell wall 18 is separated from the digits 12 and 14 by a narrow gap 20. The gaps 15 and 20 between and above the digits 12 and 14 are made as narrow as practicable to avoid accidental contacts of opposing digits or coverage of any electrode surface by the wall 18 and to allow for the required flow of the test gas through the AGS.

With the WE and the CE serving as two sensing electrodes that are close to one another as the analyte passes through the sensor in their vicinity, then electrodes 11 and 13 perform the oxidation reaction 1 and the reduction reaction 2 of Table 1, respectively. Thus, an analyte molecule R is changed to its oxidized form X at electrode 11 and then back to the original analyte molecule R at electrode 13. If the sensor is designed so that the distance between the electrodes is small as in a micro-structured or even nano-structured interdigitized electrode array, then these reactions can occur repeatedly many times to the same molecule. An analyte molecule that is exposed to this new AGS electrode structure or geometry will be continuously changing back and forth and back again, producing electrons at each reaction site us it proceeds through the interdigitized electrode array. It will thus produce many more electrons than in the simple AGS, it will produce a cascade of electrons and therefore an amplified signal.

In the presently used AGS, an analyte molecule comes into contact with the sensor interface, causes a change to occur, and this change is detected. A sensor typically requires many molecules to get a detectable change. The sensor of FIG. 3 opens the possibility for a single molecule to cause many [possibly even a million] reaction events so that a single molecule's presence might be detected.

Therefore, the basic idea of this invention is that reversible redox analyte systems can be isolated and even created in the gas phase reactions of the AGS so that detection occurs amperometrically with a greatly increased sensitivity. Femtomolar detection becomes realizable with a gas sensor structure which allows redox cycling of the analyte molecules. Such an "amplifying chemical gas sensor" has not been constructed heretofore nor has an AGS been previously able to achieve sensitivities into the femtomolar range or below.

Figure 5:
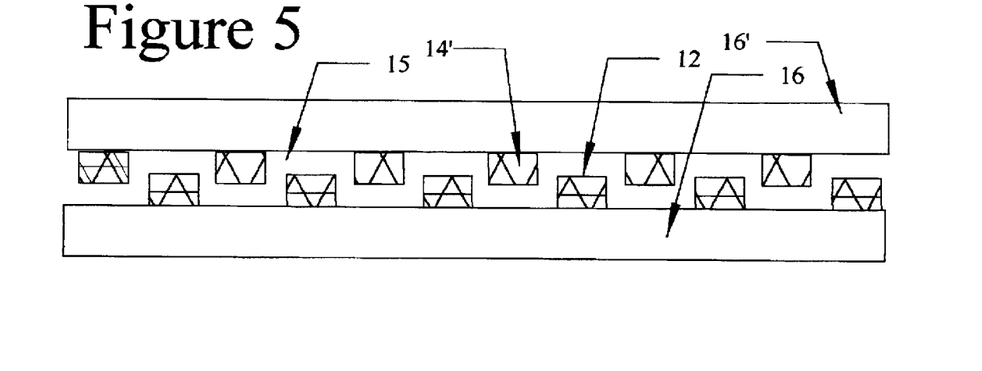
FIG. 5 is a schematic view of Section A—A' of FIG. 3 in another preferred embodiment.
Figure 6:
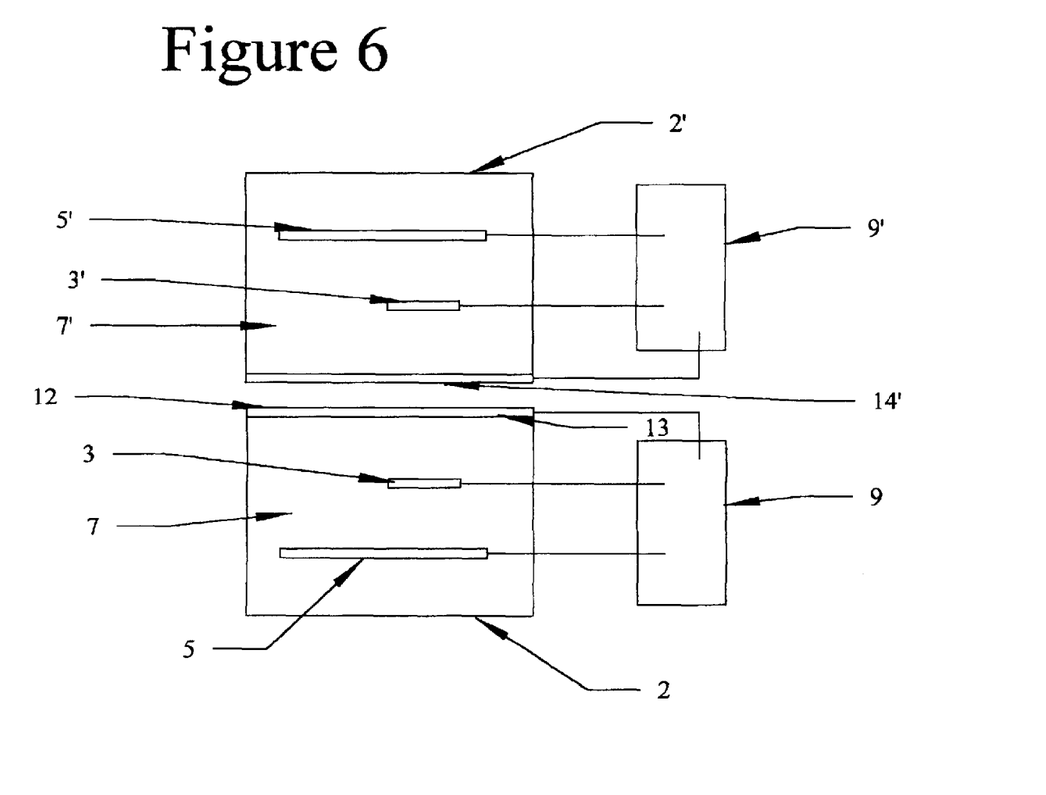
FIG. 6 is a schematic diagram of the embodiment of FIG. 5.

An alternative way of achieving the above-disclosed amplification is indicated in FIGS. 5 and 6. Referring back to FIG. 3, in lieu of the CE 13 with its digital extensions 14, the embodiment of FIG. 5 uses a second working electrode 13' with its digital extensions 14', all of which are affixed to a substrate 16' which may be similar to the first working electrode substrate 16 of FIGS. 4 and 5 and appertaining to a second AGS system. As shown in FIG. 6, the WEs 13 and 13' with their respective digital extensions 12 and 14' may be affixed to two similar sensor bodies 2 and 2' which are facing each other so as to form the interdigitized structure of FIGS. 3 and 5. The other components 3', 5', 7', and 9' may be identical or similar to the respective components 3, 5, 7, and 9 of FIGS. 1 and 6.

As an illustrative example of the application of the embodiments of FIGS. 3–6 we may begin with the redox couple $NO/NO_2$ in $N_2$ or in air with Au electrodes. The $NO/NO_2$ gaseous species is important to measure in physiological, industrial, and environmental fields.

For a gas sensor with dual electrodes of Au in a lock and key geometry, as illustrated in FIGS. 3–6, the electrodes may be vapor deposited onto Nafion with cooling of the substrate and slow thermal deposition or sputtering of the Au. Rapid evaporation or lack of cooling causes substrate damage and poor adhesion. Lock-and-key electrodes have been used in other devices and sensors such as SAW and chemiresistor sensors but not in the amperometric toxic gas sensor. And, lock-and-key configurations have never been used to gain chemically amplified signals in the AGS as disclosed here. In this invention, the geometry is intended to cause each single molecule entering the detector to yield a significantly amplified signal. This amplification of the detector signal makes it possible to increase sensitivity by several orders of magnitude.

The crux of the new structures is that the operation of the two electrodes is complementary. The linearly complementary redox electrodes are adjusted so that one is set at a potential of >1.0 V vs RHE in acid electrolyte to perform oxidation of NO to $NO_2$ while the other is at a potential of 0.8 V vs RHE in acid electrolyte to perform reduction of $NO_2$ to NO. In the resulting electrochemical system the redox reactions 5 and 6 of Table 1 are the substantive ones. Thus when an $NO_2$ molecule enters the detector, it produces a reduction current at electrode 11 and its digital extensions 12, and the resulting NO molecule diffuses to the nearby oxidizing digits 14 or 14' of electrode 13 or 13' generating an anodic current and an $NO_2$ molecule. This process occurs again and again as the gas sample proceeds through the narrow channels 15 and 20 of the gas exposure chamber along or across the interdigitated electrodes. This process is so fast that there is significant time for gaseous diffusion and electrochemical reaction to occur. This situation can be easily achieved as long as a good catalyst is used for the electrochemical reactions and the diffusion distance is short, so that residence times are long when compared to the flow rate. The flow rate will determine how long the analyte remains in contact with the structured electrodes. In the embodiment of FIGS. 5 and 6, the NON $O_2$sensor designed in this way has the absolute values of the outputs of the working electrodes summed [one a reduction and one and oxidation] resulting in a constructive interference with each other and an "amplified" signal for the entering NO or $NO_2$ in the sampled gas.

A single molecule can proceed along the sample gas path producing electrons as long as it is near the electrodes. If the electrodes are close together, the same analyte molecule of NO or NO2 that enters the detector, will, over time, elicit multiple electrons from each sensing electrode. The number will depend upon the rate of the electrochemical process and the time to diffuse between each electrode. To minimize any losses from processes such as oxidation to $NO_3^-$ or diffusion into the solution and away from the reaction zone, the electrodes should be preferably microfabricated so that interdiffusional distances are small [of micron dimensions]. Sub-millimeter electrodes may be constructed using an ink-printing technique or by lithographically defined vapor deposition of electrodes having dimensions of about 100 microns so as to minimize the loss processes.

A simple calculation can illustrate the possible gain for such an "amplified" amperometric gas sensor system. Gaseous diffusion is of the order of $10^5$ cm/sec so that about a microsecond is all that passes between exposure of the analyte from one site to the next electrode site when the electrodes are as much as 1 mm apart. Let us assume that the reactions can also occur in a microsecond and the gas path is constructed so that it has a volume of 1 cc and is operated at a flow rate of 1 cc/second. Then the analyte has a residence time of 1 second and the molecule has the chance to react around $10^6$ times. This produces an amplification of the gas phase concentration of $10^6$ times that of a single electrode reaction. In principle, if the traditional AGS can detect 5 ppb $NO_2$ in air, this new AGS of FIGS. 3–6 could potentially measure 5 ppq of $NO_2$ in air.

These estimates are only exemplary. We can envision many geometries and systems that could be complementary and create new and useful "amplified" AGSs. Other new structures can be envisioned. Circular or ring electrode paths and redox reactions that are in equilibration between a solution and a gaseous species are but two more examples. A third example is an array of electrode dots that are addressable individually or in subsets such that they can perform the function of either the oxidation or reduction reactions. These configurations would also be able to accomplish the above enhancement, and there may be some others possible in three dimensions that would be covered in this same general class.

Of course the sensitivity of such a system will be lower if the reaction rate and diffusion rates in the electrodes and electrolytes are slower than assumed above. Also, some of the molecules may diffuse into the electrolyte solution and not directly into the gas phase from the triple phase boundary. This would cause a slower diffusion between electrodes. Further there may be non-faradaic or parasitic reactions, such as the formation of $NO_3^-$ or other chemical side reactions, which may cause some of the analyte to be lost near one of the electrodes.

If the losses are from dissolution into the electrolyte, thin-film electrolytes can be employed to minimize them. If the loss is from oxidation of NO to $NO_3^-$ instead of $NO_2$, one can select the optimum electrolyte and electrode potential for conversion to $NO_2$. The parasitic processes may therefore be addressed by using techniques that include different catalysts, very thin film electrolytes, and control of electrode potentials.

Additional benefits and information can be derived from having two complementary electrodes to react with an analyte redox pair. Even if the digits of the complementary electrodes of FIGS. 3–6 are made identical in composition, structure, and geometry, they will not really be exactly symmetrical in their redox chemistries for many reasons. We could consider these electrodes as electrochemically anisotropic surfaces. In a traditional AGS, we would use a single catalyst and simply see a sensor signal from the analyte. Now, the structures of FIGS. 3–6 lead to anisotropic currents on the side by side complementary electrodes which need to be adjusted by changing the composition, width or electrode potential of one set of the complementary digits. This opens new ways of detecting an analyte with maximum selectivity. A gas sensor which produces a specific current symmetry if a particular redox couple is present, is identifying that redox couple to the exclusion of others. This greatly increases the information content produced by the complementary electrode surfaces. Reactions take place over time in a non-uniform manner. Additional information can thus be gained by following the constructive interference [ox-redox] and any destructive interference as reactions proceed on electrochemically anisotropic surfaces toward equilibrium. As in classical analytical amperometry and voltammetry, adjustments of electrode potentials can be used to facilitate or extinguish gas phase reactions at the complementary electrodes. For example, only the redox couple will produce the anodic and cathodic current with a symmetry based on their relative reaction rates. If an interference enters and can only be reduced or oxidized, an unsymmetrical current will be produced. In fact if the $NO/NO_2$ reaction rates are not tuned to be the same, the reaction which is faster will dominate and one would observe an ever decreasing rate for the faster reaction as it consumes the reactant and an ever increasing rate for the slower reaction as the concentration builds. One can envision many different scenarios here but the point is that the two-electrode system will contain some selectivity information beyond that of the simple single electrode system. Such information may be useful in identifying a redox pair. The same information also relates to identifying interferences in sensor signals and sorting out an analyte signal from those of interferences or identifying and quantifying multiple analytes in a mixture.

Although our foregoing discussion pertained mainly to the $NO/NO_2$ couple, similar properly adjusted interdigitated sensors can, of course, serve to detect other redox couples. For example, a similar amplification mechanism can be effectuated with chlorine to chloride and vice versa using Pt rather than Au electrodes.

Other "amplifying" gas and liquid sensors can be developed with the principles disclosed herein. The same principles may be applied to the sensing of many other analytes, such as oxygen, CO, $NH_3$, ethanol, unsaturated hydrocarbons, and other electroactive gases and vapors. The above materials and structures can be combined into more and different complex designs than are described here. The disclosed improvements can be incorporated into microfabrication, micro-electro-mechanical systems [MEMS], and other gas sensors. The AGS described herein may also be part of an instrument, coupled to a sampling system and/or a computer data interpretation system to gather and interpret the improved qualitative and quantitative information produced by this new AGS.

There will now be obvious many variations and modifications of the afore-disclosed embodiments to persons skilled in the art. All of these variations and modifications will remain within the scope of this invention if defined by the following claims.

I claim:

1. Amperometric sensing apparatus for detecting an analyte in a gaseous medium, winch comprises:

a working electrode at which said analyte is caused to participate in an analyte half-cell reaction;

a reference electrode for controlling the electrochemical potential of said working electrode;

a counter electrode at which a complementary half-cell reaction is caused to occur, wherein all three electrodes are electrochemically connected through an electrolyte and said counter and reference electrodes may be combined into a single electrode;

means of enhancing the reactivity of the counter electrode to the product of the analyte reaction; and means for reconverting the product of the analyte reaction back to the analyte and then reacting it again at the working electrode, with such back-and-forth reactions repeating many times, so as to yield an amplification of the analyte signal.

2. The apparatus of claim 1, wherein said reconversions are caused to occur at the counter electrode.

3. The apparatus of claim 2, wherein said sensing apparatus is designed or tuned for reconversion and detection of the $NO-NO_2$ or $Cl-Cl_2$ redox couple.

4. The apparatus of claim 2, wherein said working and counter electrodes are interdigitated or comprise an array of electrodes which are addressable in subsets.

5. Amperometric sensing apparatus for detecting an analyte in a gaseous medium, which comprises:

a first working electrode at which said analyte is caused to participate in an analyte half-cell reaction; and a second working electrode for reconverting tho product of the analyte reaction back to the analyte; and means for reacting said product again at the first working electrode, with such back-and-forth reactions repeating many times, so as to yield an amplification of the analyte signal, each of said working electrodes being electrochemically connected to its respective pair of counter and reference electrodes;

wherein each of said pairs of counter and reference electrodes may be combined into a single electrode.

6. The apparatus of claim 5, wherein the first of said working electrodes is designed or tuned for detection of NO or Cl species, with the second working electrode optimized for detection or identification of the corresponding oxidizing species, $NO_2$ or $Cl_2$.

7. The apparatus of claim 5, wherein said working electrodes are interdigitated.

8. A method of detecting the presence of an analyte or trace thereof in a gaseous medium comprising the steps of:

passing a sample of said gaseous medium over a pair of interdigitated electrodes forming part of an amperometric gas sensor system, while applying an oxidizing potential to one electrode of said pair and a reducing potential to the other electrode of said pair, so as to cause repeated oxidations and reductions of said analyte and of its redox product and thereby produce amplified current signals due to said analyte and product;

measuring said amplified current signals; and deducing the presence or identity or concentration of said analyte in said gaseous medium from said measured current signals.

9. The method of claim 8, wherein said analyte and product comprise the $NO-NO_2$ or $Cl-Cl_2$ redox couple.

10. Sensing apparatus for detecting an analyte in a gaseous medium, which comprises:

means for passing a sample of said gaseous medium over a pair of interdigitated electrodes forming part of an amperometric gas sensor system, while applying an oxidizing potential to one electrode of said pair and a reducing potential to the other electrode of said pair, so as to cause repeated oxidations and reductions of said analyte and of its redox product and thereby produce amplified current signals due to said analyte and product; and means for measuring said amplified current signals.

11. The apparatus of claim 10, wherein said gaseous medium may be separated from said electrodes solely by a thin layer of electrolyte.

12. The apparatus of claim 10, comprising more than one of said pairs or an array of electrode pairs that are addressable individually or in subsets, each of which can perform oxidation-reduction reactions for a different analyte.

13. The apparatus of claim 10, comprising counter and reference electrodes that are inaccessible to or inactive towards said analyte.

14. The apparatus of claim 10, comprising means for deducing from said amplified signals the identity or concentration of said analyte.

15. The apparatus of claim 10, wherein both of said respective pairs of counter and reference electrodes are substantially identical or similar.

16. The apparatus of claim 10, wherein said counter and reference electrodes are inaccessible to or inactive towards said analyte.

* * * * *